United States Patent [19]

Pacifici et al.

[11] 4,043,887

[45] Aug. 23, 1977

[54] BENZOPHENONE INITIATORS FOR THE PHOTOPOLYMERIZATION OF UNSATURATED COMPOUNDS

[75] Inventors: James G. Pacifici; Richard H. S. Wang; Gordon C. Newland, all of Kingsport, Tenn.

[73] Assignee: Eastman Kodak Company, Rochester, N.Y.

[21] Appl. No.: 759,688

[22] Filed: Jan. 17, 1977

[51] Int. Cl.$^2$ ............................ C08F 2/46; C08F 4/00
[52] U.S. Cl. ............................ 204/159.23; 96/115 P; 204/159.15; 204/159.18; 204/159.19; 260/476 R; 260/591
[58] Field of Search ............... 204/159.23, 159.18; 96/115 P; 260/476 R, 591

[56] References Cited

U.S. PATENT DOCUMENTS

| 3,686,084 | 8/1972 | Rosenkranz et al. | 204/159.15 |
| 3,988,228 | 10/1976 | Newland et al. | 204/159.23 |

*Primary Examiner*—Richard B. Turer
*Attorney, Agent, or Firm*—Elliott Stern; Daniel B. Reece, III

[57] ABSTRACT

This invention relates to 3,4-bis(halomethyl) benzophenone photoinitiators and these initiators admixed with unsaturated photopolymerizable compounds. When such compositions are irradiated by ultraviolet light, the benzophenone derivatives split off free radicals which initiate the photopolymerization of the unsaturated photopolymerizable compounds.

3 Claims, No Drawings

BENZOPHENONE INITIATORS FOR THE PHOTOPOLYMERIZATION OF UNSATURATED COMPOUNDS

It is known that the photopolymerization of unsaturated compounds can be substantially accelerated by initiators. Furthermore, it is known that initiators having the following structural formula have utility in the photopolymerization of unsaturated compounds in which $R^1 = -CH_2X$, $CHX_2$, $CX_3$; $R^2 = H$, $CH_3$, $CH_2X$, $CHX_2$, $CX_3$; $X$ = chlorine, bromine or iodine.

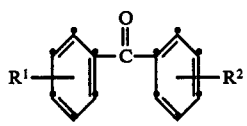

These compositions are more fully discussed in U.S. Pat. No. 3,686,084. The photoinitiators useful in the practice of this invention are structurally related to the above composition, yet exhibit unexpected and unobvious properties over these known photoinitiators. Aromatic ketones substituted with a halomethyl group in the 4- position (U.S. Pat. Nos. 3,686,084 and 3,988,228) are efficient photoinitiators for the polymerization of acrylic monomer systems. When these systems are irradiated in the presence of air, however, the rate of polymerization is significantly retarded. We have found that the presence of halomethyl groups on both the 3- and 4- position of one of the aromatic rings initiates the polymerization of the unsaturated monomer system in air at a rate significantly greater than the compositions disclosed in the above references. This effect is unexpected and unobvious, and cannot be attributed to the fact that two halomethyl groups are present, since benzophenones containing halomethyl groups on each of the aromatic rings of benzophenone are not nearly as effective in air as the novel compounds of this invention. The observed effect, i.e., that of increased activity in air, cannot be explained by the presently available technology. The observed effect is of high practical significance in view of the decreased need to carry out coating application in an inert atmosphere. The discovery of the activity in air, therefore, represents a significant advance in the art.

Accordingly, there is provided a composition comprising a photopolymerizable unsaturated compound having admixed therewith, as a photopolymerization initiator, about 0.1 to about 10% by weight, based on the weight of the unsaturated compound, of at least one benzophenone derivative of the formula

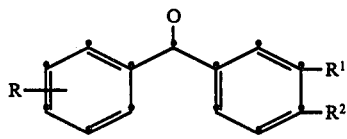

wherein R is hydrogen, chloro, methoxycarbonyl, methyl, t-butyl; and $R^1$ and $R^2$ are the same or different and each is $-CH_2X$, $CHX_2$, or $CX_3$ wherein X is chloro or bromo. Examples of such benzophenone derivatives which exhibit the highly advantageous characteristics of the invention are 3,4-bis(chloromethyl)benzophenone, 3,4-bis(chloromethyl)-4'-carbomethoxy benzophenone, 3,4-bis(chloromethyl)-4'-chlorobenzophenone, 3,4-bis-(bromomethyl)benzophenone, 3,4-bis(dichloromethyl)benzophenone.

These compounds are primarily characterized by their universal applicability and by their high reactivity to all photo-polymerizable substances, especially under the influence of long wave ultraviolet light. In general, they are used in amounts of about 0.1 to about 10, preferably about 0.5 to about 2% by weight, based on the unsaturated compounds. The most effective rays for initiating the polymerization are those with wavelengths from 2,500 to 4,000 A. Suitable light sources besides sunlight are therefore mainly mercury, tungsten, and xenon lamps, as well as certain fluorescent lamps.

The ethylenically unsaturated compounds useful in the present invention can be, for example, lower alkyl and substituted alkyl esters of acrylic and methacrylic acid. Examples of such esters include: methyl methacrylate, ethyl methacrylate, 2-ethylhexyl methacrylate, isobutyl methacrylate, butyl acrylate, 2-ethylhexyl acrylate, 2-hydroxyethyl acrylate, 2-methoxyethyl acrylate, 2-hydroxypropyl acrylate, and the like. Also useful are polyacrylyl compounds represented by the general formula:

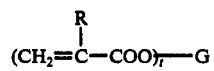

R is hydrogen or methyl; G is a polyvalent alkylene group of the formula $-C_xH_{2x}-y-$ in which $x$ is 2 to 10 and $y$ is 0 to 2 [e.g., (a) divalent alkylene such as $C_xH_{2x}$ when $y = 0$, i.e., $-C_2H_4$-, $-C_3H_6$-, $-C_5H_{10}$-, neo-$C_5H_{10}$ and the like; (b) trivalent alkylene such as $C_xH_{2x}$-1 when $y = 1$, i.e.,

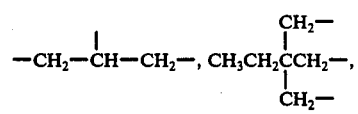

and the like; or (c) tetravelent alkylene such as $C_xH_{2x-2}$ when $y = 2$,

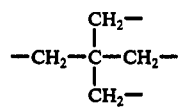

and the like); a divalent $(C_rH_{2r}O)_tC_rH_{2r}$- group in which $t$ is 1 to 10 (e.g., oxyethylene, oxypropylene, oxybutylene, polyoxyethylene, polyoxypropylene, polyoxybutylene, polyethylene-oxypropylene, $-CH_2C(CH_3)_2COOCH_2C(CH_3)_2CH_2$-, etc.); and r is the valence of G and can be from 2 to 4. Also useful are allyl arcylates and methacrylates; e.g., allyl methacrylate, and allyl acrylate. Other unsaturated compounds useful in the invention are vinyl acetate, vinyl and vinylidine halides; e.g., vinyl chloride, vinylidine chloride; amides, e.g., acrylamide, diacetone acrylamide; vinyl aromatics, e.g. stryrene, alykl styrenes, halostyrenes, and divinyl benzenes. The ethylenically unsaturated, photocurable compounds also include acrylate-capped or acrylate-terminated oligomers such as acrylate-capped urethane and epoxy resins.

In addition, other unsaturated compounds which can be photopolymerized by using the initiators of this invention are unsaturated polyester resins which are known in the art. Such polyesters may be prepared by reaction of α,β-unsaturated dicarboxylic acids can be replaced by saturated dicarboxylic acids or aromatic dicarboxylic acids, e.g., isophthalic acid and the like. Polyhydric alcohols are preferably dihydric alcohols such as ethylene glycol, however, trihydric and polyhydric alcohols such as trimethylolpropane can also be conjointly used. Examples of such α,β-unsaturated dicarboxylic acids or their anhydride counterparts include maleic, fumaric, itaconic and citraconic and the like.

The above unsaturated compounds can be used alone or as mixtures of such compounds or mixtures in combination with other unsaturated components and the like.

The photoinitiators may be added at any time in the production of the photopolymerizable compositions in amounts conventionally used for photoinitiators. They are generally used in amounts of from 0.01 to 10%, preferably in amounts of from 0.5 to 3% by weight, based on the weight of the light-sensitive compositions.

Conventional thermal inhibitors which are used in the production of light-sensitive compositions, for example, hydroquinone, p-methoxy phenol, t-butyl hydroquinone, may also be used in the conventional manner in the light-sensitive compositions of this invention to alter the curing rates and/or to provide longer storage stability.

The photopolymerizable compositions of the present invention may also contain other additives, pigments, colorants, stabilizers and the like. For example, polymeric compositions, such as unsaturated polyesters may also contain and generally do contain other additives such as white or colored pigments or colorants, antioxidants, plasticizers, flow aids, processing aids, polymeric modifiers and the like.

This invention will be further illustrated by the following examples, although it will be understood that these examples are included merely for purposes of illustration and are not intended to limit the scope of the invention.

EXAMPLE 1

Synthesis of the novel compounds was carried out according to the following method. Benzoic acid (1.68 moles) was added to 3.96 moles of o-xylene and 0.6 mole POCl$_3$ and refluxed at 140° C. for 11 hours. The reaction product was cooled to room temperature, washed once with 500 ml. of water, twice with 300 ml. of 5% of Na$_2$CO$_3$ and twice again with 500 ml. of water. After washing, the xylene was distilled and the residue was vacuum distilled to obtain 3,4-dimethylbenzophenone. A mixture of 3,4-dimethylbenzophenone (1.0 mole), benzoyl peroxide (5 grams), chlorobenzene (800 ml.) and 3.0 moles of sulfuryl chloride was heated at 90° C. for 3½ hours. During the last 30 minutes of the reaction nitrogen was passed through the reactor to remove the excess sulfuryl chloride. The resultant mixture was cooled and 50 grams of carbon black was added and the mixture stirred for 30 minutes, after which the carbon black was removed by filtration. The product 3,4-bis(chloromethyl)benzophenone was isolated by stripping of the solvent. Analysis found: 62.1% C, 4.3% H, and 27.1% Cl. Theoretical: 64.5% C, 4.3% H, and 25.5% Cl.

EXAMPLE 2

3,4-Bis(chloromethyl)benzopheone and other representative compounds needed for comparison were dissolved in distilled neopentyl glycol diacrylate at 2(w/w)% concentration. Evaluation of the compounds as photoinitiators was made by photocalorimetry. This technique consists of recording the exotherms generated by successive flashes of light on the sample while it is on the stage of a DSC (Differential Scanning Calorimeter, Perkin-Elmer DSC-1B). The light source was a Bausch & Lomb mercury lamp, SP-200, and it was situated such that the light evenly illuminated the sample and references stages of the DSC. A photographic shutter was interposed between the lamp and DSC stage. A sample (10 mg.) of the composition to be tested was placed on the stage which is thermostatically controlled to a constant temperature of 25° C. Air was used as the sample atmosphere. The composition was irradiated with successive 10 second flashes of light and the corresponding exotherm for each light period recorded. This was continued until no exotherm was observed. The area under each exotherm was integrated and the percent of the total exotherm plotted versus irradiation time. The velocity constant, $k_{obs}$, is the observed rate constant for the polymerization of the α,β-unsaturated composition, neopentyl glycol diacrylate. It is defined as $$k = \frac{2.303}{t} \log \frac{a}{a - x}$$

where $x$ is the amount of monomer reacting in time $t$, $a-x$ is the amount remaining after tine $t$. (*Outlines of Physical Chemistry*, Farrington Daniels, John Wiley and Sons, Inc. p. 346.)

The values of k are customarily taken as rate values to indicate the extent of reaction with time. In this case, $k_{obs}$ is the extent of polymerization with irradiation time. Calibration of the DSC to measure calories allows one to also measure heat of polymerization (ΔH) in terms of K Cal./mole of monomer. The results of photocalorimetry measurements are shown in Table 1. The superiority of 3,4-bis(chloromethyl)benzophenone over known haloalkyl ketones is readily evident by comparison of the relative rates. The compound of this invention is 3–13 times better than those disclosed in U.S. Pat. No. 3,686,084.

EXAMPLE 3

A comparison of the effectiveness of 3,4-bis(chloromethyl)benzophenone and 4,4'-bis(chloromethyl)benzophenone was made in a series of α,β-unsaturated monomers. The compounds were dissolved in the monomers at 2(w/w)% and photocalorimetry measurements made as described in Example 2. The results of the evaluation, summarized in Table 2, indicate that 3,4-bis(chloromethyl)benzopheone is from 40% to 366% better than 4,4'-bis-(chloromethyl)benzophenone.

EXAMPLE 4

Compounds to be evaluated were mixed at 2(w/w)% with Cargill Acrylate Resin XP-9041, an acrylate-capped urethane monomer. Specimens were evaluated by the photocalorimetry method described in Example 2 in an air atmosphere. The results, summarized in Table 3, indicate that 3,4-bis(chloromethyl)benzophenone is superior to those specific compounds described in U.S. Pat. No. 3,686,084.

TABLE 1

| Photocalorimetry of Neopentyl Glycol Diacrylate in Air | | | |
|---|---|---|---|
| Photoinitiator at 2% | Relative Rates[a] | $k_{obs.}$ | ΔH (KCal/mole) |
| 3,4-Bis(chloromethyl)benzophenone | 13.6 | 0.068 | 4.9 |
| 4,4'-Bis(chloromethyl)benzophenone | 4.0 | 0.020 | 4.7 |
| 4-Chloromethylbenzophenone | 3.6 | 0.018 | 4.0 |
| 4,4'-Bis(bromomethylbenzophenone) | 1.0 | 0.005 | 2.2 |

[a]Normalized on 4,4'-bis(bromomethyl)benzophenone

TABLE 2

| Comparison of Photoinitiators in Various Monomers | | | | | |
|---|---|---|---|---|---|
| | | Photoinitiator A | | Photoinitiator B | |
| Monomer | % Increase of A over B | $k_{obs.}$ | ΔH (KCal/mole) | $k_{obs.}$ | ΔH (KCal/mole) |
| Trimethylolpropane triacrylate | 42.8 | 0.04 | 3.0 | 0.028 | 2.9 |
| 3-Hydroxypropyl acrylate | 52.0 | 0.038 | 4.0 | 0.025 | 4.0 |
| 2-Methoxyethyl acrylate | 366.0 | 0.014 | 3.0 | 0.003 | 1.9 |
| Diethylene glycol diacrylate | 133.0 | 0.133 | 6.5 | 0.057 | 6.6 |

Photoinitiator A = 3,4-Bis(chloromethyl)benzophenone
Photoinitiator B = 4,4'-Bis(chloromethyl)benzophenone

TABLE 3

| Evaluation of Photoinitiator in Acrylate Polymer | |
|---|---|
| Photoinitiator at 2% Concn. | $k_{obs.}$ |
| 4,4'-Bis(chloromethyl)benzophenone | 0.12 |
| 4-Chloromethylbenzophenone | 0.09 |
| 3,4-Bis(chloromethyl)benzophenone | 0.17 |

The invention has been described in detail with particular reference to certain preferred embodiments thereof, but it will be understood that variations and modifications can be effected within the spirit and scope of the invention.

We claim:

1. A composition comprising a photopolymerizable ethylenically unsaturated compound having admixed therewith, as a photo-polymerization initiator, about 0.1 to about 10% by weight, based on the weight of the unsaturated compound, of at least one benzophenone derivative of the formula

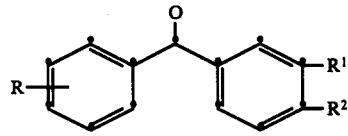

wherein
R is hydrogen, chloro, methoxycarbonyl, methyl, t-butyl, and $R^1$ and $R^2$ are the same or different and each is -$CH_2X$, $CHX_2$, or $CX_3$ wherein X is chloro or bromo.

2. The composition of claim 1 wherein R is hydrogen or chloro; and each $R^1$ is $CH_2Cl$.

3. The composition of claim 1 wherein R is hydrogen; $R^1$ is $CHCl_2$; and $R^2$ is $CHCl_2$.